(12) United States Patent
Lewis et al.

(10) Patent No.: US 7,251,031 B2
(45) Date of Patent: Jul. 31, 2007

(54) COLORSTICK

(75) Inventors: M. Anthony Lewis, Mahomet, IL (US); Ralph Etienne-Cummings, Washington, DC (US); Kaijen Hsiao, Waltham, MA (US); Ilyas M. Ayub, Villa Grove, IL (US); Viktor Gruev, Baltimore, MD (US); Chris F. Milne, Urbana, IL (US)

(73) Assignee: Iguana Robotics, Inc., Urbana, IL (US)

( * ) Notice: Subject to any disclaimer, the term of this patent is extended or adjusted under 35 U.S.C. 154(b) by 0 days.

(21) Appl. No.: 11/040,191

(22) Filed: Jan. 24, 2005

(65) Prior Publication Data

US 2005/0280823 A1 Dec. 22, 2005

Related U.S. Application Data

(60) Provisional application No. 60/538,310, filed on Jan. 23, 2004.

(51) Int. Cl.
*G01N 21/25* (2006.01)

(52) U.S. Cl. ...................................... 356/407; 356/406

(58) Field of Classification Search ................ 356/402, 356/406, 407, 408, 425, 326, 328; 358/509, 358/514
See application file for complete search history.

(56) References Cited

U.S. PATENT DOCUMENTS

| | | | | |
|---|---|---|---|---|
| 4,140,220 A * | 2/1979 | Hazeltine et al. | ........... | 209/580 |
| 5,137,364 A * | 8/1992 | McCarthy | ................... | 356/402 |
| 5,229,841 A * | 7/1993 | Taranowski et al. | ........ | 356/406 |
| 5,377,000 A * | 12/1994 | Berends | ........................ | 356/73 |
| 5,537,211 A * | 7/1996 | Dial | ............................ | 356/402 |
| 5,690,486 A * | 11/1997 | Zigelbaum | .................... | 433/29 |
| 5,704,612 A * | 1/1998 | Kelly et al. | ................. | 273/402 |
| 6,020,583 A * | 2/2000 | Walowit et al. | .............. | 250/226 |
| 6,124,936 A * | 9/2000 | Okamoto | ..................... | 356/406 |
| 6,157,454 A * | 12/2000 | Wagner et al. | .............. | 356/407 |
| 6,457,644 B1* | 10/2002 | Collins et al. | ......... | 235/462.14 |
| 6,466,321 B1* | 10/2002 | Satake et al. | ................ | 356/402 |
| 6,512,577 B1* | 1/2003 | Ozanich | ........................ | 356/73 |
| 6,535,287 B1* | 3/2003 | Matsui et al. | ................ | 356/406 |
| 6,583,880 B2* | 6/2003 | Berstis | ........................ | 356/407 |
| 6,590,659 B2* | 7/2003 | Melnyk et al. | .............. | 356/406 |
| 6,674,530 B2* | 1/2004 | Berstis | ........................ | 356/406 |
| 6,683,680 B2* | 1/2004 | Dinu et al. | ................... | 356/30 |
| 6,798,517 B2* | 9/2004 | Wagner et al. | .............. | 356/406 |
| 2004/0043350 A1* | 3/2004 | Jung et al. | ..................... | 433/29 |

* cited by examiner

*Primary Examiner*—Layla G. Lauchman
(74) *Attorney, Agent, or Firm*—Whitham, Curtis, Christofferson & Cook, PC

(57) ABSTRACT

A device comprising an illumination means and a light sensing means, that can examine and memorize a discrete color of an object based on the magnitude of the reflected light bouncing off of the colored surface in at least three areas of the electromagnetic spectrum. The device also provides output as a visually and/or audibly perceptible signal for deciphering the color. The color range identified by the device is not limited to the visible spectrum and may include infra-red and ultra-violet light. A storage means for memorizing colors may also be included in the device. Applications of ColorStick technology may include children's toys, aids for the visually handicapped (e.g. blind or color blind individuals), designers, internet shoppers, gardeners, etc.

20 Claims, 4 Drawing Sheets

COLORSTICK

CROSS-REFERENCE TO RELATED APPLICATIONS

This application claims priority of U.S. Provisional Patent Application 60/538,310, filed Jan. 23, 2004, which is hereby incorporated by reference in its entirety.

BACKGROUND OF THE INVENTION

1. Field of the Invention

The present invention generally relates to a color sensor, and, more specifically to a color sensor linked to a speaker device, haptic display, and/or visual display, audibly, tactilely, and/or visually identifying the color detected by the color sensor.

2. Description of the Prior Art

Determining the true color of an object, without the subjectivity and error of an individual can be difficult as many people see and interpret colors differently. For a blind person or a person with true color blindness (seeing only values, but no hues), the task is impossible. Other conditions, such as red-green color blindness, also make the task of proper color identification difficult. Further, the color that any given object may appear can change based on various lighting situations, depending on the time of day or weather conditions if the object is in natural light, or if the object is viewed in a room with incandescent or fluorescent lighting. Further, the color of the object may appear to change depending upon the color of other objects in the environment, and the reflected light of such an object influencing the color of another object. As such, the viewing of color can be very subjective, and often confusing.

In such a circumstance where one color is difficult to identify, the task of identifying multiple colors and then determining the aesthetic appeal of their use in combination with each other is nearly impossible. For individuals with color blindness, or for people who need to match colors in a variety of lighting conditions, such as decorators, a tool that could aid in the color determining and/or matching process could be a valuable asset.

Many devices and arrangements for color analysis are known, such as in the photographic industry and particularly for color printing and color matching in manufacturing. However, these devices must be capable of measurement of a continuum of color and are usually complicated, bulky, expensive and difficult to calibrate. Therefore such devices are generally unsuitable for the applications noted above and many others.

SUMMARY OF THE INVENTION

It is therefore an object of the present invention to provide a method of accurately identifying magnitudes of reflected light (both inside and outside the range of the visible spectrum) independent of the lighting conditions in which the object is located and providing a result in a manner easily assimilated by a user and of enhanced usefulness.

In order to accomplish these and other objects of the invention, a color recognition device will be provided comprising a light shield for excluding ambient light, an illuminator, and a light sensor, wherein the illuminator or the light sensor comprise a plurality of bandwidth-limited devices operating at different regions of the electromagnetic spectrum, the illuminator and the light sensor cooperating to detect a magnitude of reflected light in each in different regions of the electromagnetic spectrum. A storage arrangement for storing a response corresponding to selected combinations of magnitudes of reflected light in different regions of the electromagnetic spectrum and an output arrangement for providing output response(s) as a perceptible visual, tactile, and/or audible signal(s) are also included.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF A PREFERRED EMBODIMENT OF THE INVENTION

Figure 1:
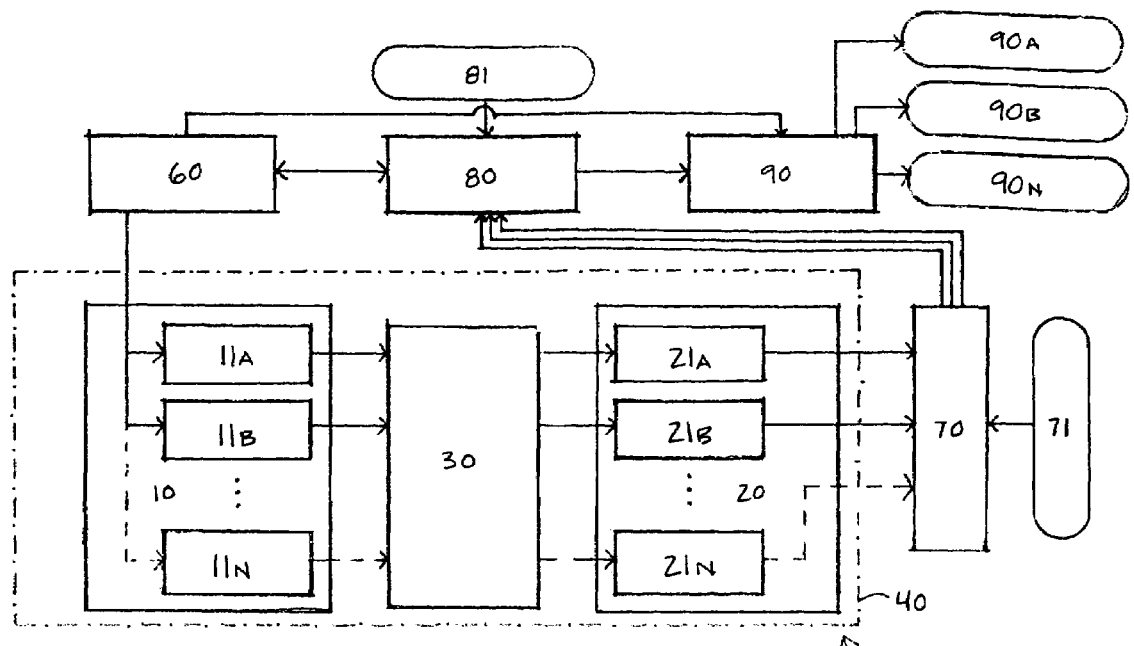
FIG. 1 is a block diagram of an embodiment of the invention wherein both the illumination arrangement and the light sensing arrangement have a plurality of bandwidth-limited devices operating at different regions of the electromagnetic spectrum.

Referring now to the drawings, and more particularly to FIG. 1, there is shown a block diagram of the invention wherein both the illumination arrangement 10 and the light sensing arrangement 20 have one or more bandwidth-limited devices 11a–c, 21a–c operating at different regions of the electromagnetic spectrum. The illumination arrangement 10 may comprise three or more different colored LED light sources or other sources of bandwidth-limited illumination 11a, 11b, 11n. The light sources are not limited to the visual range and may include infra-red and ultraviolet regions and used with a broad band sensor. The light source 10 may also be a single white light source used with similarly bandwidth-limited sensors. The light sensing arrangement 20 can be one or more photosensor 21a, 21b, 21n, having a bandwidth-limiting spectral sensitivity. The preferred way of implementing the spectral sensitivity is by use of a color filter 21a, 21b, 21n, between the illuminated surface 10 and the sensor 20.

To ensure an accurate record of an object's color, individually or for comparison to other objects, the illumination arrangement 10, paired with the light shield 40, shows the color 30 of an object where all conditions are equal to any other color record on the device, despite the given environment of the colored object. The light shield 40 isolates all of the color sensitive aspects of the color recording process (such as the illumination arrangement 10, the light sensing arrangement 20, and the colored surface being recorded 30) such that the only light under which the colored surface 30 is viewed is the light provided by the illumination arrangement 10. As shown in FIG. 1, all components shown within the bounds of the light shield 40 may sometimes be collectively referred to as the color sensing head 100.

A control device 60 is provided to activate the illumination arrangement 10, and begin the color sensing process. In a configuration where the illumination arrangement 10 comprises more than one color of light, serving as a plurality of bandwidth-limiting devices 11a, 11b, 11n, the control device 60 may be used to expose each bandwidth individually, in specific combinations, or all at once, depending on the informational needs of the user and sensor configuration. The light sensor 20 sense the reflected light 31a, 31b, 31n off of the colored surface and reports the component color information (averaged for a patterned surface) to the processing circuit 70. The light sensor 20 may consider the reflected light 31a, 31b, 31n input all at once, or through a plurality of bandwidth-limited photosensors 21a, 21b, 21n.

Figure 4:
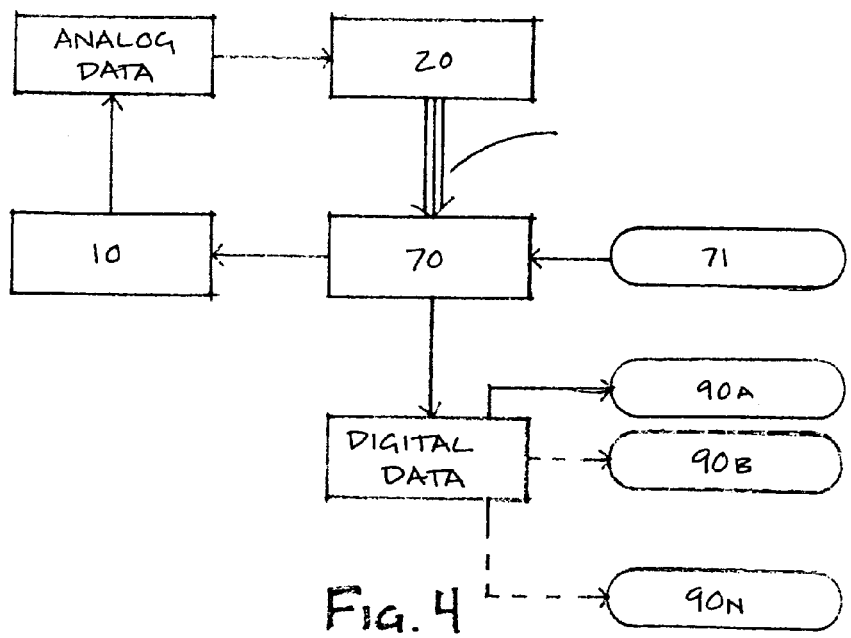
FIG. 4 is a block diagram showing the conversion of data from analog to digital.
Figure 5:
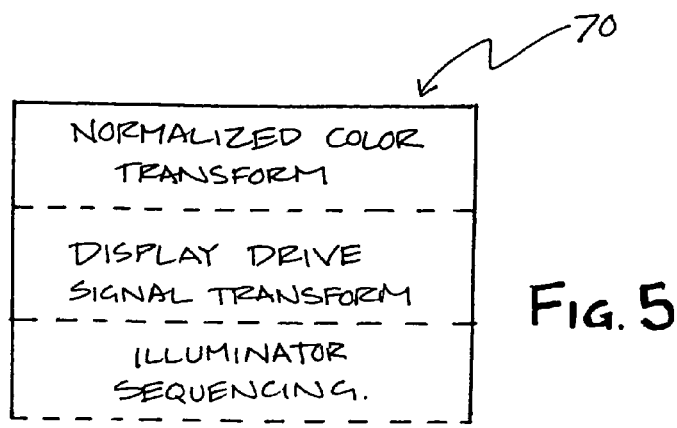
FIG. 5 is a block diagram showing the different possible functions of the processor circuit.
Figure 7A:
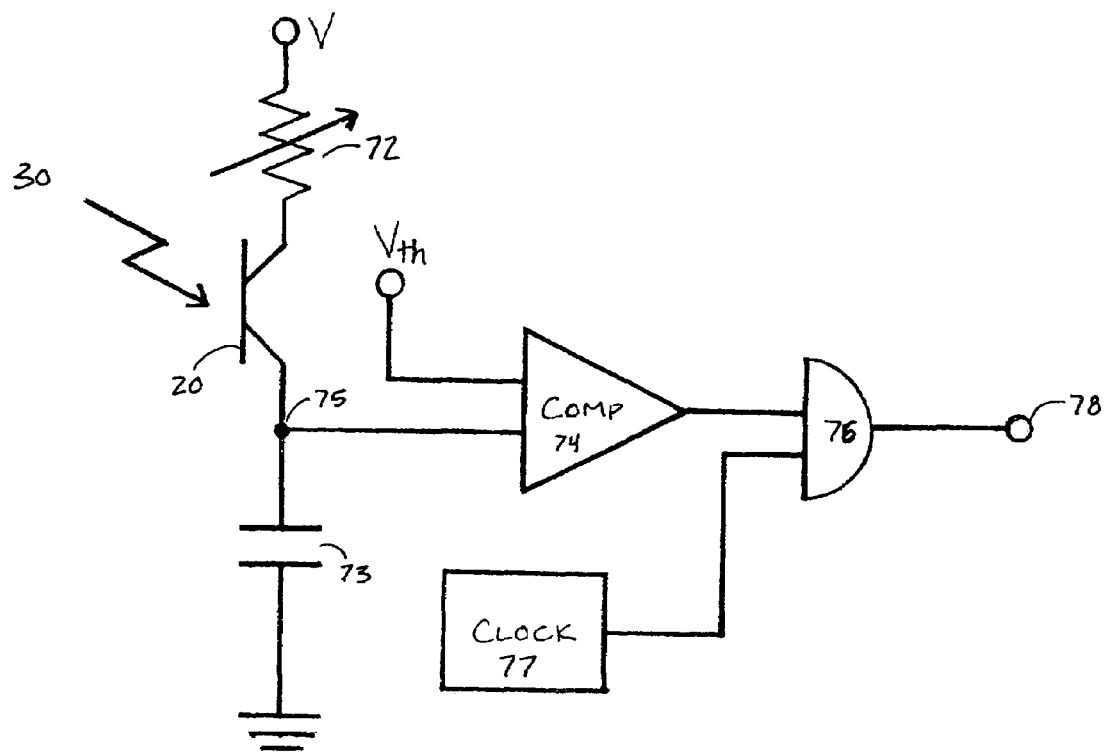
FIGS. 7A and 7B are an exemplary measurement circuit and a depiction of the response thereof, respectively.
Figure 7B:
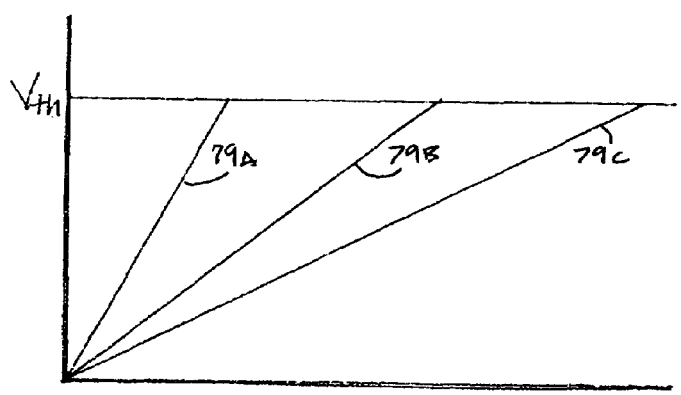

The processing system 70, further illustrated in FIG. 4 and FIG. 5, has either of two preferred implementations. First, as shown in FIG. 4, an analog data to digital data conversion device, possibly of a commercially available type, that converts the current or electrical signal from the photosensor (s) 20 to a digital signal and can control the light source(s) 10 is included in a preferred embodiment of the invention. A particularly preferred and simple expedient for deriving a digital signal from the analog sensor output is shown in FIG. 7A. In the circuit illustrated, a photosensor 20 (shown in the form of a phototransistor is connected in series with a resistor 72 and a capacitor 73. The resistor 72 is preferably a variable resistor and can be adjusted for calibration. A comparator 74 is connected to a node 75 between the sensor 20 and the capacitor 73 and the output of the comparator 74 is used as an input to a logic circuit 76 schematically depicted as an AND gate which also receives an input from a clock circuit 77. The function of the logic circuit 76 is not critical to the practice of the invention and may be arranged to provide several logic outputs as may be needed (e.g. for discharging the capacitor, controlling the light source(s) and the like). As will be readily understood by those skilled in the art, the magnitude of the light flux incident on the sensor controls the amount of current which flows to the capacitor and the voltage developed due to charging of the capacitor will increase at a corresponding rate, as depicted, for example at 79a, 79b or 79c in FIG. 7B. While the voltage on the capacitor 73 is below a threshold voltage Vth, also applied to the comparator 74, the logic circuit 76 will pass the clock pulses to output 78 but will block the clock pulses once the capacitor voltage reaches the threshold voltage Vth (and other control functions exercised). Thus, the number or count of clock pulses will accurately reflect, in a digital form, the light flux incident on the sensor.

A suitable digital processing circuit 70, microcontroller 70, or digital logic system 70 may be used to implement an algorithm 71 for converting the photosensor 20 information to a hue and saturation value 90. As shown in FIG. 5, the digital circuit contains suitable logic for normalizing color values, display drive signaling, and turning the light sources on and off in proper sequence in the case of multiple illumination sources or briefly illuminating the light source in the case of multiple photosensors so as to save power. Referring back to FIG. 1, a storage element 80 is included to memorize discrete colors, or combinations of colors, is included in the preferred embodiment of the invention. The device may recognize, for example, a series of pre-memorized colors loaded into the memory system 80. For example, the memory device may associate classifications of an object color 30 with a color title (e.g. "red," "green," or "blue"). The memory system 80 uses predetermined arbitrary response inputs 81 which, depending on the presence and constitution of such a storage element, provide the desired output signals(s) 90. Potential outputs 90 of this device include at least one of a audible output 90a describing the color (e.g. by color name, pigment mix formula or the like), a visual display 90b showing the color, or a numeric representation 90n of the color in a suitable, machine readable format (i.e. a rs-232 connection), or a haptic display that can deliver information via touch to a user.

The second possible implementation of the processing system 70 is the fabrication of a VSLI chip. This chip would integrate the color sensing head with the processing, and would output a signal in some form that represents color. Such an implementation may include two or more phototransistors 21a, 21b, 21n, with suitable spectral bandwidth-limited masks, and a provision for switching on an illumination source 10.

The algorithm 71 for converting sensed value to a color, located within the processing circuit 70, can be accomplished by use of an analytical equation in the case that all properties of the light source 10, the spectral masks 21a, 21b, 21n, and the characteristics of the electrical circuit are known precisely. This information can support conversion of the raw sensor output to normalized color values in a standard format, drive signals for a color display and the like. Alternatively, a neural network, lookup table, or other classification scheme can be used to accomplish this conversion after suitable training.

Figure 6:
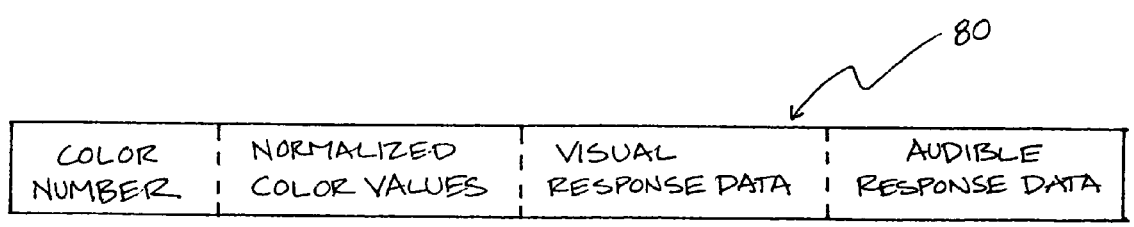
FIG. 6 shows a diagram of an exemplary memory data format.

The storage system 80 reacts to the output from the processor 70 in order to produce one or more output signal 90. The storage system, as detailed in FIG. 6, may memorize audible codes for a voice synthesizer or tone generator, or colors to drive a data cycle modulated LED or LCD display or the like.

Figure 2:
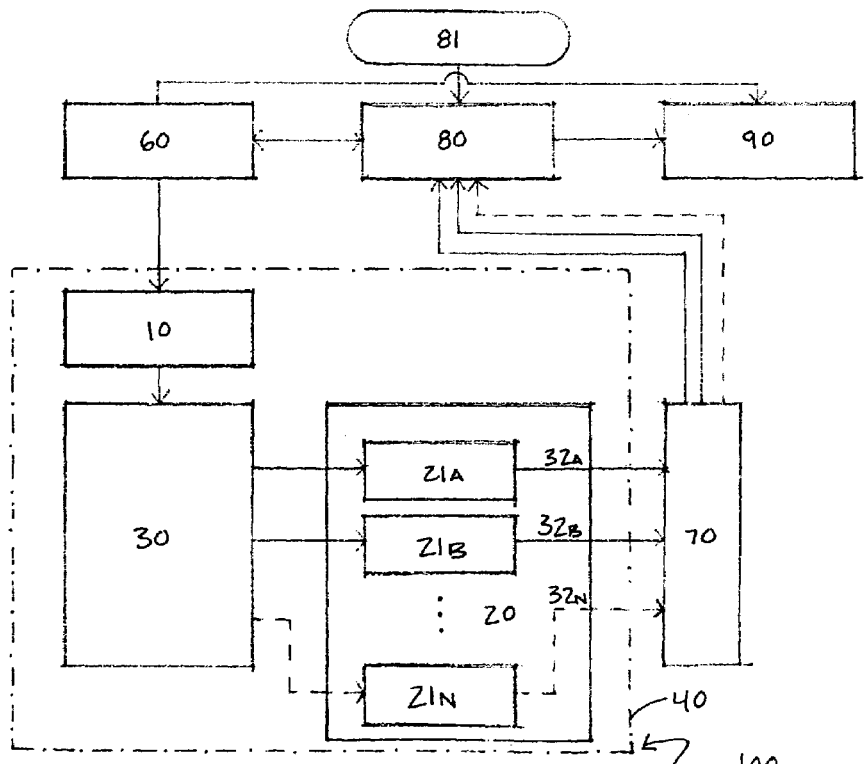
FIG. 2 is a block diagram of an embodiment of the invention wherein the light sensing arrangement has a plurality of bandwidth-limited devices operating at different regions of the electromagnetic spectrum.

FIG. 2 shows a variation of the system shown in FIG. 1 wherein there is a single illumination arrangement 10 (i.e. a single white light) wherein the light sensor 20 has three bandwidth-limited devices 21a, 21b, 21n, each detecting a the magnitude of reflected light in a different regions of the electromagnetic spectrum. The three magnitudes 32a, 32b, 32n detected by the light sensor 20 are each communicated to the processing circuit 70 and then to the memory lot 80, wherein the magnitudes are identified by an output method 90 individually or in combination. While memory organization and constitution are not critical to the practice of the invention it is preferred for simplicity to configure the memory as a look-up table so that the sensor output magnitudes 32a, 32b, 32n can be used as a direct address into memory. It should also be appreciated that the memorization of discrete colors rather than measurement over a continuum of colors provides great increase in economy as well as substantial convenience of use and usefulness of output.

Figure 3:
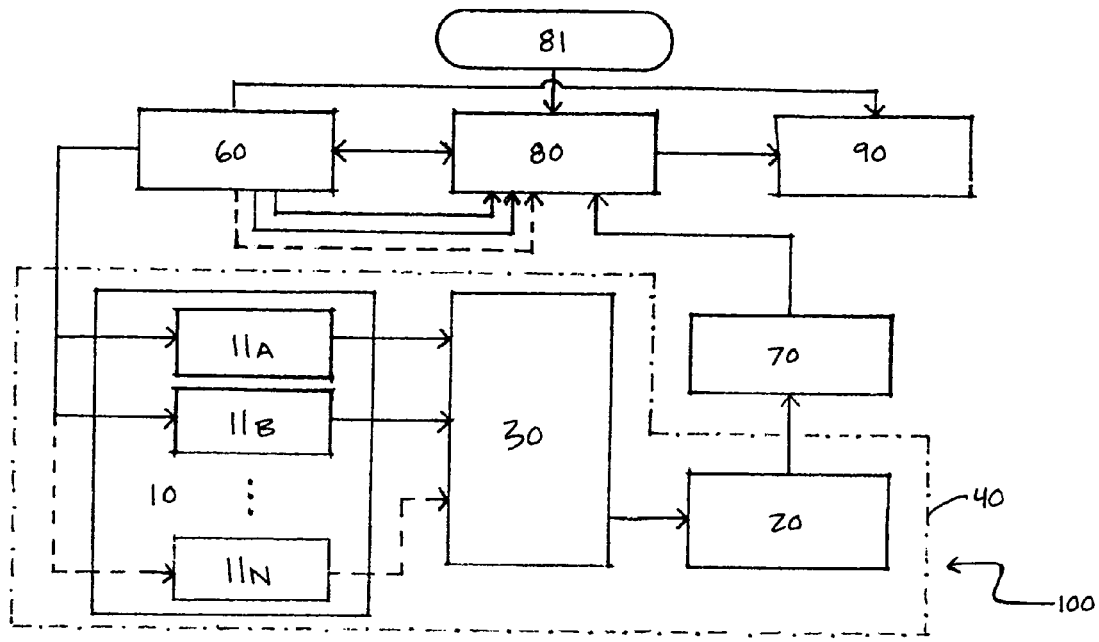
FIG. 3 is a block diagram of an embodiment of the invention wherein the illumination arrangement has a plurality of bandwidth-limited devices operating at different regions of the electromagnetic spectrum.

FIG. 3 also shows a variation of the system shown in FIG. 1 wherein there is a single light sensing arrangement 20 (i.e. a broadband light sensor) wherein the illumination arrangement 10 comprises three or more bandwidth-limited different colored LED light sources 11a, 11b, 11n, each illuminating the colored surface in a specified lighting condition, or collectively illuminating the surface 30, to display the magnitudes of the color in various regions of the electromagnetic spectrum. The properties are detected by the light sensor 20, and the information is transferred to the processing circuit 70 and then to the memory lot 80, wherein the magnitudes are identified by an output method 90 either individually or in combination.

It is important to recognize that the regions of the electromagnetic spectrum that are being examined are not limited to the visual range and may include infra-red and ultra-violet light. One possible implication for examining the infra-red range is the analysis of plant health. It has been suggested that the spectrum of plants in the infra-red range shifts when a plant is under stress (diseased, dehydrated, etc.). If a pattern of spectrum shift can be identified, the invention might be used by home gardeners, plant researchers, plant nursery workers, and others to evaluate the health of their plants based on signals (physically invisible to humans) that are exhibited by their plants.

In view of the foregoing, the self-contained device described is capable of memorizing an arbitrary number of particular colors and identifying and/or reporting or reproducing them. This device, referred to by the inventors as a "ColorStick," has many possible and valuable applications.

For example, a very practical use for the ColorStick would be for people with color blindness or even total blindness. Similar to the detection of otherwise unrecognized infra-red information in plants, color blind individuals cannot always recognize colors within the visual range of the electromagnetic spectrum. As approximately 20% of males have some degree of color blindness. Particularly for these men, the colors within a wardrobe are indecipherable. Left to their own devices, they are likely to dress themselves in a way that may appear uncoordinated in the eye of someone with "normal" vision. The ColorStick could be used to enable a color blind/fully blind person to dress himself (or herself) with more confidence by confirming and matching clothing from an existing wardrobe. Of course the option is sometimes available to consult someone with "normal" vision, however, such dependence can be a significant handicap when individually shopping for clothes or other items. The color challenged shopper is likely unaware that the purchased items don't match with each other, or with currently owned items. A ColorStick could be used to memorize colors in a persons wardrobe (or within their house, if shopping for housewares, furniture, fabrics, or paint). At the store, the saved colors on the ColorStick could be matched to the colors of items in the store.

Quite similarly, designers and decorators could use the ColorStick to match colors that are seen under different lighting conditions, as colors can look different in different lighting conditions. Decorators could memorize colors of furniture or fabric items in a home and then match this color against furniture or fabric items in a store. The system might be augmented with a high quality color display to show the match between different items. Further, color chips can be memorized by brand, and/or recognized according to family (e.g. registering multiple hues as "yellow"). Responses may be organized to reflect compatible or coordinated different colors or families of colors.

The ColorStick also has great potential for internet shoppers. When shopping online, the color of an object as displayed on a website is unreliable. Merchandise displayed online, must first be photographed (in one light), then is typically digitally altered (creating more room for color deviation) and then finally displayed on a computer screen. As computer screen displays vary in color presentation, this factor alone is enough to be wary of online ordering when the color of an item is of particular importance to the shopper (clothes, furniture, makeup, etc). Through these several factors, it is highly unlikely that the item received in the mail appears exactly the same color as it appeared on the screen. To combat this problem, the merchandiser could use the ColorStick to memorize and encode the actual color information of the product that they are selling. A potential consumer can cross check the ColorStick information posted by the merchandiser on their own ColorStick, wherein the ColorStick has a sophisticated control selection. Alternatively, a shopper might memorize a color or combination of colors in the shoppers home and then send this information to an Internet vendor who could in turn customize the color of their articles to exactly match the shoppers home.

The ColorStick can also be used as a toy. Particularly for children in the 2–5 year old age range, this toy seems like magic! Children can find hours of activity by holding the ColorStick against an object 30, pressing a button 60, and hearing the ColorStick say the object's color 90, preferably in a friendly human voice. Parents are likely to favor this stimulating, high-tech tool because it reinforces basic color and language skills, and keeps kids engaged in play. Further, the output describing the color can be presented in a variety of languages, to break language barriers, or provide an entertaining and/or educational experience for people of all ages.

As a toy, the invention could also be implemented in a game, involve music (e.g. the output for a color is a musical note, or series of notes), or determine the closest crayon color for a given object to add a fun and interesting aspect to drawing from life. As a handheld toy, the ColorStick is approximately the size of a small flashlight. Children can interact with the toy individually or in groups to learn colors and color families as well as basic language skills in a fun, dynamic way. Other applications and uses of the invention will be apparent to those skilled in the art.

While the invention has been described in terms of a single preferred embodiment, those skilled in the art will recognize that the invention can be practiced with modification within the spirit and scope of the appended claims.

We claim:

1. A color recognition device comprising
    a light shield for excluding ambient light during color recognition operation of said color recognition device,
    illumination means,
    light sensing means, at least one of said illumination means and said light sensing means comprising a plurality of bandwidth-limited devices operating at different regions of the electromagnetic spectrum, said illumination means and said light sensing means cooperating to detect magnitude of reflected light in respective ones of said different regions of said electromagnetic spectrum and encode said magnitude of reflected light as a computer readable digital or analog value defining a time between two events,
    an algorithm for converting output of said light sensing means to at least one of normalized color values in a standard format and drive signals for a color display,
    a storage means for storing a response corresponding to selected combinations of magnitude of reflected light in said different regions of said electromagnetic spectrum, said storage means storing discrete color information which is addressable in accordance with one of said magnitude of reflected light detected by said light sensing means and said normalized color values which is transformed by said algorithm to said standard format, and
    an output means for providing said response as a perceptible signal.

2. A color recognition device as recited in claim 1, wherein said storage means stores a signal to provide an audible response.

3. A color recognition device as recited in claim 2, wherein said audible response includes a variety of languages.

4. A color recognition device as recited in claim 2, wherein said audible response is generated by a voice synthesizer.

5. A color recognition device as recited in claim 2, wherein said audible response is generated by a tone generator.

6. A color recognition device as recited in claim 5, wherein said tone generator produces a musical tone.

7. A color recognition device as recited in claim 2, wherein said audible response includes a musical sound or a sequence of musical sounds corresponding to a respective colors.

8. A color recognition device as recited in claim 1, wherein said storage means stores a numeric representation response.

9. A color recognition device as recited in claim 8, wherein said numeric representation response is a signal in a machine readable format.

10. A color recognition device as recited in claim 1, wherein said storage means stores a signal to provide a tactile response.

11. A color recognition device as recited in claim 1, wherein said storage means stores a response which is organized to reflect compatible or coordinated colors or families of colors.

12. A color recognition device as recited in claim 11, wherein said storage means stores a response which facilitates the matching or coordinating of clothing.

13. A color recognition device as recited in claim 11, wherein said storage means stores a response which facilitates the matching or coordinating of housewares or furniture.

14. A color recognition device as recited in claim 11, wherein said storage means stores a response which facilitates the matching or coordinating of paints or pigments.

15. A color recognition device as recited in claim 11, wherein said storage means stores a response which controls display of a stored color.

16. A color recognition device as recited in claim 1, further including means for providing an input to control display of a color.

17. A color recognition device as recited in claim 1, wherein said storage means stores a response which corresponds to a game.

18. A color recognition device as recited in claim 1, wherein said different regions of the electromagnetic spectrum include at least one of infrared and ultraviolet.

19. A color recognition device as recited in claim 18, wherein a said response relates to a living organism.

20. A color recognition device as recited in claim 1, wherein a said response relates to a living organism.

* * * * *